US00PP19941P2

(12) United States Plant Patent
Roberson

(10) Patent No.: US PP19,941 P2
(45) Date of Patent: Apr. 21, 2009

(54) ***LANTANA* PLANT NAMED 'ROBPWCHP'**

(50) Latin Name: *Lantana camara*
Varietal Denomination: Robpwchp

(76) Inventor: Robert J. Roberson, 31706 E. Pink Hill Rd., Grain Valley, MO (US) 64029

( * ) Notice: Subject to any disclaimer, the term of this patent is extended or adjusted under 35 U.S.C. 154(b) by 0 days.

(21) Appl. No.: 12/070,565

(22) Filed: Feb. 19, 2008

(51) Int. Cl.
*A01H 5/00* (2006.01)

(52) U.S. Cl. ..... Plt./227

(58) Field of Classification Search ..... Plt./227
See application file for complete search history.

*Primary Examiner*—Annette H Para
*Assistant Examiner*—June Hwu
(74) *Attorney, Agent, or Firm*—C. A. Whealy

(57) ABSTRACT

A new and distinct cultivar of *Lantana* plant named 'Robpwchp', characterized by its semi-mounding and outwardly spreading plant habit; vigorous growth habit; dense medium green-colored leaves; freely flowering habit; and yellow and pastel apricot-colored flowers that are held above and beyond the foliage.

1 Drawing Sheet

Botanical designation: *Lantana camara.*
Cultivar denomination: 'Robpwchp'.

BACKGROUND OF THE INVENTION

The present invention relates to a new and distinct cultivar of *Lantana,* botanically known as *Lantana camara,* and hereinafter referred to by the name 'Robpwchp'.

The new *Lantana* is a product of a planned breeding program conducted by the Inventor in Grain Valley, Mo. The objective of the breeding program is to create new freely-flowering and vigorous *Lantana* cultivars with outwardly spreading habit and attractive flower coloration.

The new *Lantana* originated from a cross-pollination made by the Inventor in August, 2002 in Grain Valley, Mo. of the *Lantana camara* cultivar Robpatcow, disclosed in U.S. Plant Pat. No. 12,450, as the female, or seed, parent with the *Lantana camara* cultivar Robpathon, disclosed in U.S. Plant Pat. No. 10,011, as the male, or pollen, parent. The new *Lantana* was discovered and selected by the Inventor as a single flowering plant within the progeny of the stated cross-pollination in a controlled environment in Grain Valley, Mo. in May, 2003.

Asexual reproduction of the new *Lantana* by vegetative cuttings in a controlled environment in Grain Valley, Mo. since October, 2003, has shown that the unique features of this new *Lantana* are stable and reproduced true to type in successive generations.

SUMMARY OF THE INVENTION

The cultivar Robpwchp has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Robpwchp'. These characteristics in combination distinguish 'Robpwchp' as a new and distinct cultivar of *Lantana:*

1. Semi-mounding and outwardly spreading plant habit.
2. Vigorous growth habit.
3. Dense medium green-colored leaves.

4. Freely flowering habit.
5. Yellow and pastel apricot-colored flowers that are held above and beyond the foliage.

Plants of the new *Lantana* can be compared to plants of the female parent, the cultivar Robpatcow. Plants of the new *Lantana* differ from plants of the cultivar Robpatcow in the following characteristics:

1. Plants of the new *Lantana* are larger and more vigorous than plants of the cultivar Robpatcow.
2. Plants of the new *Lantana* are not as mounding as plants of the cultivar Robpatcow.
3. Plants of the new *Lantana* have larger and lighter green-colored leaves than plants of the cultivar Robpatcow.
4. Flowers of plants of the new *Lantana* are paler in color than flowers of plants of the Robpatcow.

Plants of the new *Lantana* can be compared to plants of the male parent, the cultivar Robpathon. Plants of the new *Lantana* differ from plants of the cultivar Robpathon in the following characteristics:

1. Plants of the new *Lantana* are less vigorous than plants of the cultivar Robpathon.
2. Plants of the new *Lantana* are not as recumbent as plants of the cultivar Robpathon.
3. Plants of the new *Lantana* have shorter internodes than plants of the cultivar Robpathon.
4. Plants of the new *Lantana* have smaller leaves than plants of the cultivar Robpathon.
5. Flowers of plants of the new *Lantana* are paler in color than flowers of plants of the Robpathon.

Plants of the new *Lantana* can be compared to plants of the *Lantana* cultivar Gold Mound, not patented. In side-by-side comparisons conducted in Grain Valley, Mo., plants of the new *Lantana* differed from plants of the cultivar Gold Mound in the following characteristics:

1. Plants of the new *Lantana* were taller and more upright than plants of the cultivar Gold Mound.
2. Plants of the new *Lantana* had larger and lighter green-colored foliage than plants of the cultivar Gold Mound.
3. Plants of the new *Lantana* had larger inflorescences than plants of the cultivar Gold Mound.

4. Plants of the new *Lantana* and the cultivar Gold Mound differed in flower color as plants of the cultivar Gold Mound had golden yellow-colored flowers.

Plants of the new *Lantana* can be compared to plants of the *Lantana* cultivar Tropical Fruit, disclosed in U.S. Plant No. 18,821. In side-by-side comparisons conducted in Grain Valley, Mo., plants of the new *Lantana* differed from plants of the cultivar Tropical Fruit in the following characteristics:

1. Plants of the new *Lantana* were more upright than plants of the cultivar Tropical Fruit.
2. Plants of the new *Lantana* had medium green-colored foliage whereas plants of the cultivar Tropical Fruit had variegated foliage.
3. Plants of the new *Lantana* had slightly larger inflorescences than plants of the cultivar Tropical Fruit.

BRIEF DESCRIPTION OF THE PHOTOGRAPHS

The accompanying colored photographs illustrate the overall appearance of the new *Lantana,* showing the colors as true as it is reasonably possible to obtain in colored reproductions of this type. Colors in the photographs may differ slightly from the color values cited in the detailed botanical description which accurately describe the colors of the new *Lantana.*

The photograph at the bottom of the sheet comprises a side perspective view of a typical flowering plant of 'Robpwchp' grown in a container.

The photograph at the top of the sheet is a close-up view of typical inflorescences and leaves of 'Robpwchp'.

DETAILED BOTANICAL DESCRIPTION

The aforementioned photographs and following observations and measurements describe plants grown in Bonsall, Calif. under commercial practice during the autumn in an outdoor nursery with day temperatures ranging from 13° C. to 38° C. and night temperatures ranging from 10° C. to 24° C. Plants used in the photographs and for the description were grown in one-gallon containers for about six weeks. In the following description, color references are made to The Royal Horticultural Society Colour Chart, 1995 Edition, except where general terms of ordinary dictionary significance are used.

Botanical classification: *Lantana camara* cultivar Robpwchp.

Parentage:

*Female, or seed, parent.*—*Lantana camara* cultivar Robpatcow, disclosed in U.S. Plant Pat. No. 12,450.

*Male, or pollen, parent.*—*Lantana camara* cultivar Robpathon, disclosed in U.S. Plant Pat. No. 10,011.

Propagation:

*Type.*—By vegetative cuttings.

*Time to initiate roots, summer.*—About 12 to 14 days at 26° C.

*Time to initiate roots, winter.*—About 15 to 17 days at 20° C.

*Time to produce a rooted young plant, summer.*—About four weeks at 26° C.

*Time to produce a rooted young plant, winter.*—About five weeks at 20° C.

*Root description.*—Fibrous; medium in thickness; white in color.

*Rooting habit.*—Freely branching; dense.

Plant description:

*Plant habit.*—Initially upright, then semi-mounding and outwardly spreading habit. Freely branching habit; about five to six primary lateral branches per plant each with numerous secondary branches; pinching enhances lateral branch development; dense and bushy plant habit. Vigorous growth habit.

*Plant height.*—About 35 cm.

*Plant diameter.*—About 50 cm by 58 cm.

Lateral branch description:

*Length.*—About 38 cm.

*Diameter.*—About 3 mm.

*Internode length.*—About 4.4 cm.

*Strength.*—Strong.

*Texture.*—Pubescent; coarse.

*Color.*—146A.

Foliage description:

*Arrangement.*—Opposite, simple.

*Length.*—About 5 cm.

*Width.*—About 3.5 cm.

*Shape.*—Ovate to lanceolate to somewhat deltoid.

*Apex.*—Acute.

*Base.*—Obtuse.

*Margin.*—Serrate.

*Texture, upper and lower surfaces.*—Coarse, rough.

*Venation pattern.*—Pinnate; arcuate.

*Color.*—Developing and fully expanded foliage, upper surface: 147A; venation, 146B. Developing and fully expanded foliage, lower surface: 147B; venation, 147D.

*Petiole.*—Length: About 8 mm. Diameter: About 1.5 mm. Texture, upper and lower surfaces: Pubescent. Color, upper and lower surfaces: 146B.

Flower description:

*Flower arrangement and habit.*—Solitary tubular flowers arranged in compact rounded axially umbels; flowers face mostly upward or outward. Freely flowering habit with potentially two inflorescences developing per node, each umbel with about 28 flowers.

*Natural flowering season.*—Spring until frost in the autumn; flowering continuous during this period.

*Flower longevity on the plant.*—About three to four days. Flowers not persistent.

*Fragrance.*—None detected.

*Inflorescence height.*—About 1.8 cm to 2 cm.

*Inflorescence diameter.*—About 4 cm.

*Flowers.*—Appearance: Flared trumpet, corolla fused, four-parted. Diameter: About 1 cm by 1.2 cm. Depth (height): About 1.8 cm.

*Flower buds.*—Length: About 1.2 cm. Diameter: About 3 mm. Shape: Elongate, oblong. Color: 39B.

*Corolla.*—Arrangement: Single whorl of four fused petals. Petal lobe length, lateral lobes: About 4 mm. Petal lobe length, upper and lower lobes: About 6 mm. Petal lobe width, lateral lobes: About 5 mm. Petal lobe length, upper and lower lobes: About 7 mm. Petal lobe shape: Rounded. Petal lobe apex: Rounded. Petal margin: Entire, slightly sinuate. Petal texture, upper surface: Smooth, glabrous; velvety. Petal texture, lower surface: Pubescent. Color: When opening, upper surface: 11B. When opening, lower surface: 39B. Fully opened, upper surface: 11C with pale tints of 54D that intensifies with development; throat and eye, 24A; color becoming closer to 23B to 23C and eventually becoming closer to 35B to 35C; towards the throat, 32A to 32C. Fully opened, lower surface: 11D with pale tints of 54D; color becoming closer to 31D.

*Calyx.*—Appearance: Short and narrow tubular calyx. Length: About 2 mm. Diameter: About 1 mm. Sepal apex: Acute. Sepal margin: Entire. Sepal texture, upper surface: Smooth, glabrous. Sepal texture, lower surface: Pubescent. Sepal color, upper surface: 145B. Sepal color, lower surface: 145A.

*Peduncles.*—Length: About 3.6 cm. Diameter: About 1 mm. Strength: Strong. Texture: Pubescent, coarse. Color: 146B.

*Pedicels.*—Length: Less than 1 mm. Diameter: Less than 1 mm. Color: Close to 146B.

*Reproductive organs.*—Stamens: Quantity/arrangement: Four per flower, adnate to floral tube. Filament length: About 2 mm. Filament color: 145D. Anther shape: Oval. Anther length: Less than 1 mm. Anther color: 162A. Pollen amount: Scarce. Pollen color: 163D. Pistils: Quantity: One per flower. Pistil length: About 3.5 mm. Stigma shape: Rounded. Stigma color: 145B. Style length: About 2 mm. Style color: 157A. Ovary color: 145A. Fruits/seed: Fruit and seed development have not been observed.

Temperature tolerance: Plants of the new *Lantana* have been observed to tolerate temperatures from about 4° C. to about 38° C.

Pathogen/pest resistance: Plants of the new *Lantana* have not been observed to be resistant to pests and pathogens common to *Lantanas*.

It is claimed:

1. A new and distinct *Lantana* plant named 'Robpwchp' as illustrated and described.

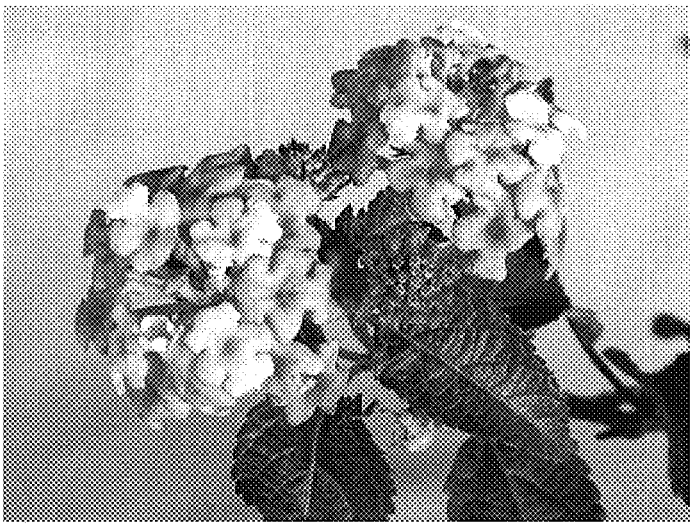
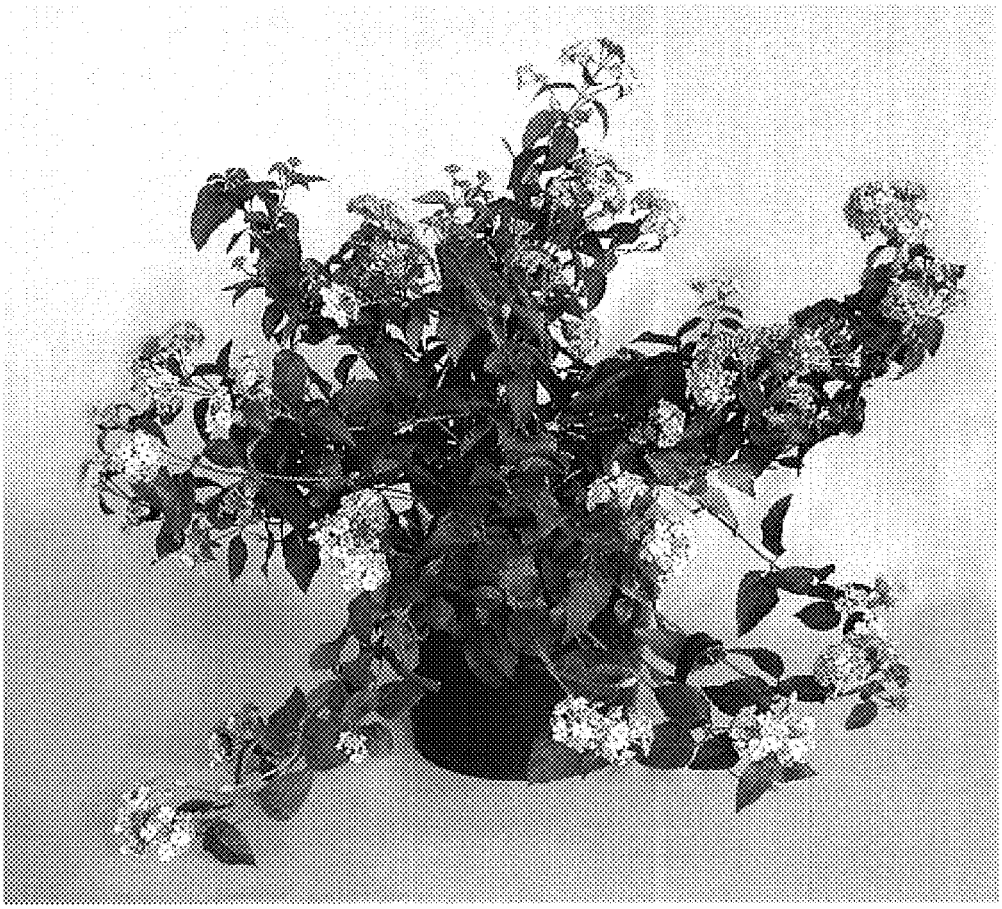

* * * * *